United States Patent [19]
Lenker

[11] Patent Number: 6,110,121
[45] Date of Patent: Aug. 29, 2000

[54] METHOD AND APPARATUS FOR OBTAINING IMPROVED RESOLUTION FROM INTRALUMINAL ULTRASOUND

[76] Inventor: Jay Alan Lenker, 408 Panorama Dr., Laguna Beach, Calif. 92651

[21] Appl. No.: 09/236,936

[22] Filed: Jan. 25, 1999

[51] Int. Cl.$^7$ .................................................. A61B 8/12
[52] U.S. Cl. ........................................ 600/463; 600/466
[58] Field of Search ..................................... 600/437, 443, 600/454, 462–463, 466–467, 471; 128/916

[56] References Cited

U.S. PATENT DOCUMENTS

| | | |
|---|---|---|
| 4,587,972 | 5/1986 | Morantie, Jr. . |
| 4,917,097 | 4/1990 | Proudian et al. . |
| 5,000,185 | 3/1991 | Yock . |
| 5,125,410 | 6/1992 | Misono et al. ...................... 600/467 X |
| 5,243,988 | 9/1993 | Sieben et al. . |
| 5,313,949 | 5/1994 | Yock . |
| 5,377,685 | 1/1995 | Kazi et al. ............................. 600/463 |
| 5,379,772 | 1/1995 | Imran ..................................... 600/467 |
| 5,405,337 | 4/1995 | Maynard . |
| 5,485,845 | 1/1996 | Verdonk et al. ....................... 600/467 |
| 5,505,088 | 4/1996 | Chandraratna et al. ............... 600/466 |
| 5,606,975 | 3/1997 | Liang et al. ........................... 600/466 |
| 5,651,366 | 7/1997 | Liang et al. ........................... 600/439 |
| 5,699,805 | 12/1997 | Seward et al. ......................... 600/459 |
| 5,720,285 | 2/1998 | Petersen ................................. 600/463 |
| 5,735,282 | 4/1998 | Hossack ................................. 600/459 |
| 5,771,896 | 6/1998 | Sliwa, Jr. et al. ...................... 600/463 |
| 5,779,643 | 7/1998 | Lum et al. .............................. 600/462 |
| 6,013,033 | 1/2000 | Berger et al. .......................... 600/466 |

OTHER PUBLICATIONS

Krulevitch, et al., Thin Film Shape Memory Alloy Microactuators, Journal of Microelectromechanical Systems, Dec. 1996, pp. 270–282 vol. 5, No. 4.

Van Urk et al., Endovascular Ultrasound, pp. 29–35, Vasular and Endovascular Surgical Techniques, 3$^{rd}$ ed RN Greenhalgh, editor, WB Saunders, London, England, 1994.

Endosonics, Solid–State Intracoronary Ultrasound. A Technology Whose Time Has Come, pp. 1–4 http://www.endosonics.com/reference/solid.htm.

Primary Examiner—Francis J. Jaworski

[57] ABSTRACT

A rotationally vibrating imaging catheter and method of utilization has an array of ultrasound transducers and an actuator along with signal processing, display, and power subsystems. The actuator of the preferred embodiment is a solid state nitinol actuator. The actuator causes the array to oscillate such that the tip of the catheter may be rotated through an angle equal to or less than 360 degrees. The tip is then capable of rotating back the same amount. This action is repeated until the desired imaging information is acquired. The rotationally vibrating catheter produces more imaging points than a non-rotating imaging catheter and eliminates areas of missing information in the reconstructed image. Rotationally vibrating catheters offer higher image resolution than stationary array catheters and greater flexibility and lower costs than mechanically rotating imaging catheters.

20 Claims, 5 Drawing Sheets

METHOD AND APPARATUS FOR OBTAINING IMPROVED RESOLUTION FROM INTRALUMINAL ULTRASOUND

FIELD OF INVENTION

This invention relates to image improvements for intravascular ultrasound (IVUS) systems.

BACKGROUND OF INVENTION

Intravascular ultrasound is a rapidly evolving imaging technique most commonly employed in coronary and iliofemoral arteries. The technique has the potential to facilitate the study of atherosclerosis and to outline the effect of endovascular intervention in more detail than angiography.

The presently used intravascular ultrasound systems fall into two categories: stationary electronic systems and mechanically driven rotating transducer systems. In both systems, an acoustic element or transducer is used to transmit a signal which impinges upon, and reflects from, surfaces of different acoustic densities which the signal encounters. An acoustic transducer receives the reflected wave. This data is sent to a processing system via an electrical cable where it is manipulated and displayed as an image.

The non-rotating or stationary catheter of the stationary electronic system houses an array of small acoustic elements which are positioned cylindrically around the catheter tip. After positioning the catheter in a vessel, body lumen or cavity, subgroups of acoustic elements may together generate an echo image. The spacing between the acoustic elements in the transducer array creates areas where the acoustic signal is neither transmitted nor received. When the data is processed, gaps of missing information occur, resulting in a poor quality image. The advantage of the stationary electronic system is that the catheter is very flexible and a central lumen is available for guidewire insertion. No distortion of the image, due to inhomogeneous mechanical rotation, is present. The stationary catheters are reliable and inexpensive but produce a poor quality image.

The mechanical intravascular ultrasound-imaging catheter comprises a mechanically rotating catheter shaft with a single ultrasound transducer. Either the acoustic element rotates or the acoustic element is stationary and a mirror rotates. In this manner the acoustic signal is transmitted and received in a continuous 360 degree sweep. There are no gaps in the data and a higher quality image results. Realizing a driving mechanism while keeping the catheter fully flexible and steerable as well as miniature are challenging problems. Distortion of the image due to an unequal rotation of the element or mirror at the catheter tip is a limitation of these systems. Advantages of the mechanical probes include high resolution imaging and absence of near field artifact. The mechanically rotating devices produce an acceptable image but are unreliable and expensive.

Both stationary electronic systems and mechanical systems typically operate with acoustic frequencies from 10 to 30 MHz.

The present invention, using a solid state actuator, is more reliable and less expensive than the rotating catheters with a single acoustic transducer. It can also easily have a central lumen for instrumentation or for a guidewire. In addition, the present invention produces a higher resolution image with fewer gaps in the information than the stationary imaging catheters. This invention creates a high resolution ultrasound image with higher reliability and less expense than is currently available. Thus, this invention fills a market demand for a high resolution, reliable and inexpensive imaging catheter.

SUMMARY OF INVENTION

The present invention is a catheter comprising an array of ultrasound transducers and an actuator along with signal processing, display, and power subsystems. The actuator on the catheter causes the array to oscillate. This allows the array to produce more imaging points of the object to be viewed than a non-rotating or a stationary array. Additional computer processing of the ultrasound data produces an image with a higher resolution than images produced from data from a non-oscillating transducer array.

The present invention comprises a catheter, which has a distal tip and a proximal end. The catheter optionally comprises a central lumen or a guidewire tip. The central lumen is often used for guidewire passage. It may also comprise additional lumens for purposes such as balloon inflation and deflation, contrast media injection, and fluid removal. The distal tip comprises an array of at least one transducer for transmitting ultrasound energy radially outward, an array of at least one transducer for receiving ultrasound signals, and an actuator. The transmitting and receiving transducers may optionally be the same physical entity. The transmitting and receiving transducers are electrically connected to the proximal end of the catheter by a transmission line, cable or wire bundle which is electrically connected to a decoder, a power generator, and a display instrument. The actuator is also electrically connected to the proximal end of the catheter with a transmission line, cable or wire bundle which is electrically connected to a power supply. The ultrasound transducer array on the distal tip of the catheter transmits and receives ultrasound signals which are processed by a computer to create an image of the object subjected to the ultrasound signals.

The distal tip of the catheter, which contains the transducer array, rotates clockwise and then counterclockwise either with the rest of the catheter or, preferably, independent of the catheter. The tip of the catheter may be rotated through an angle equal to or less than 360 degrees. Most advantageously, the tip is rotated sufficiently to fill in the information gaps but not more than required so as to minimize the requirements of the actuator. The tip is then capable of rotating backwards the same amount. The net motion is a rotating oscillation or a vibration. The oscillating distal tip may be optionally covered with a non-oscillating shield.

The present invention does not continually rotate. It vibrates rotationally in the same manner as an agitator so as to gather data to fill in the missing information between array elements. The rotating tip allows the ultrasound array to image a segment of the lumen and to move so as to fill in the information lost between array elements. This lost information between array elements is the reason stationary array systems offer less resolution than rotating transducer systems.

The preferred embodiment for vibrating or agitating the distal tip of the catheter is a nitinol actuator or set of nitinol actuators mounted so as to cause movement of the tip. When the nitinol is electrically charged, it changes dimensions due to resistive heating. When the electric charge is removed, the nitinol returns to its original dimensions. Allowance for hysteresis must be made. By counter-attaching the actuators, they can be alternately activated and deactivated causing the tip to alternately vibrate clockwise and then counterclockwise.

DETAILED DESCRIPTION OF THE INVENTION

The invention herein described is an ultrasound-imaging catheter comprising a rotationally vibrating tip and an array of ultrasound transducers. The catheter of the present invention allows the flexibility and cost effectiveness of a conventional stationary ultrasound-imaging catheter but has superior image data gathering capabilities as is illustrated in FIGS. 1, 2A, and 2B.

Figure 1:
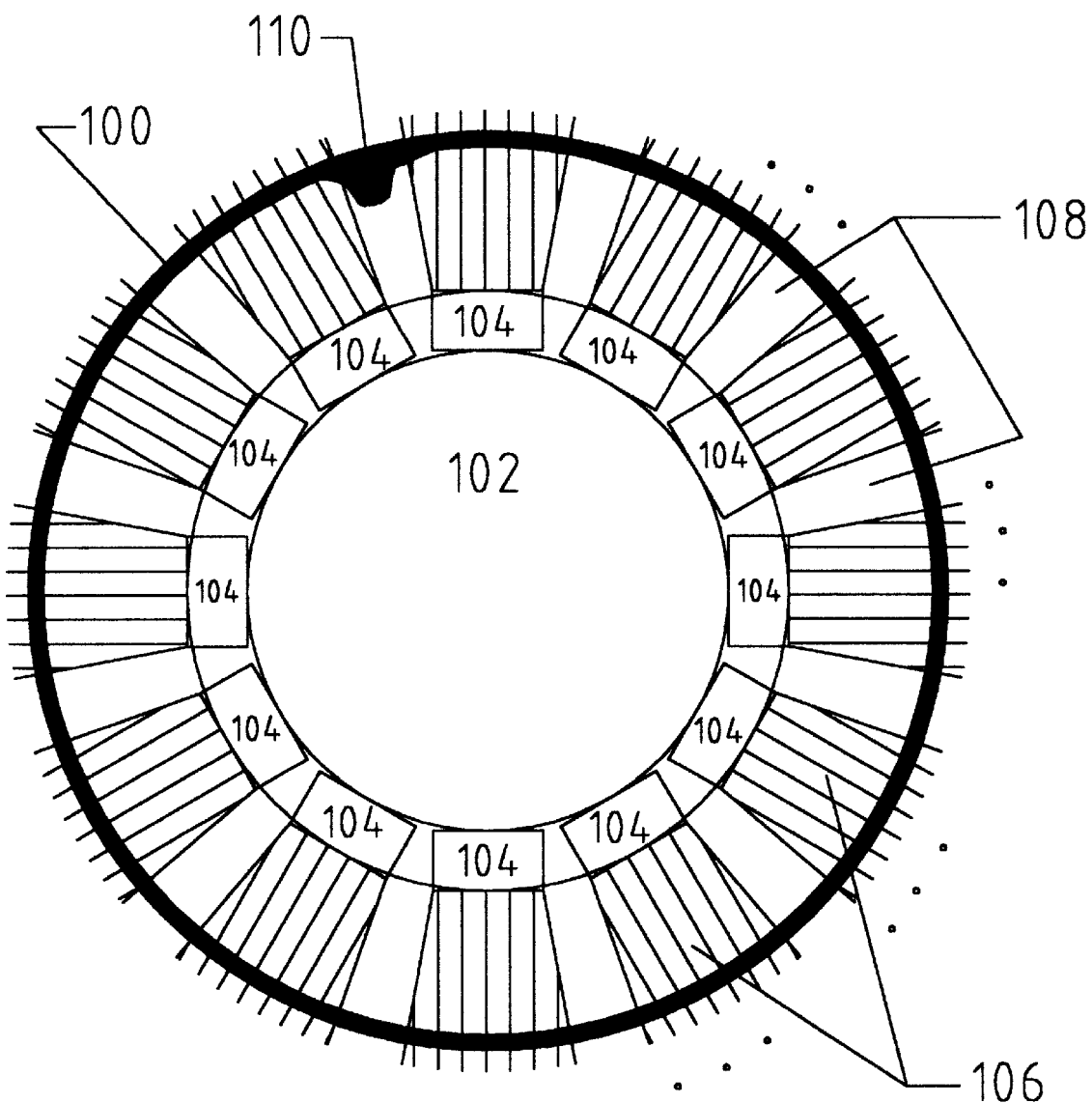
FIG. 1 shows the field of vision for a stationary imaging catheter positioned in a body lumen.

FIG. 1 illustrates, in cross section, a distal tip of a stationary imaging catheter 102 imaging a body lumen 100. The body lumen 100 has an inside surface irregularity 110. The imaging catheter 102 comprises a plurality or array of ultrasound transducers 104, a plurality of fields of view 106 and a plurality of blind spots 108. The transducers 104 are placed circumferentially around the tip 102. Each transducer 104 transmits ultrasound energy and receives reflected ultrasound energy within its field of view 106. The blind spots 108 are areas where no ultrasound energy is transmitted nor is any reflected ultrasound energy received. Most of the illustrated lumen irregularity 110 is in one of the blind spots 108. After data from the transducers 104 is processed to create a visual image, the blind spots 108 correspond to areas of no or missing information, resulting in a poor image.

Figure 2A:
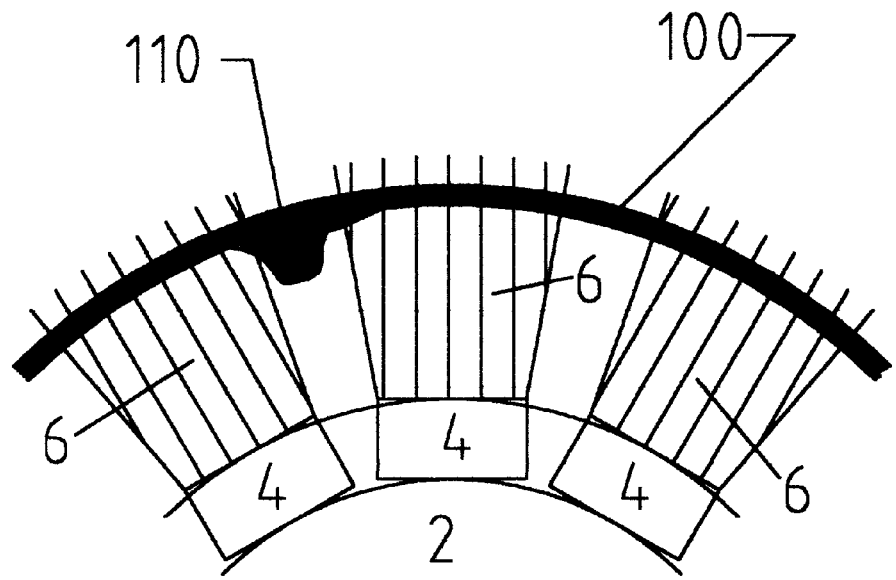
FIGS. 2A and 2B show the field of vision for a vibrating imaging catheter of the present invention, positioned in a body lumen.

Referring to FIG. 2A, a portion of a distal tip of a vibrating imaging catheter 2 images a portion of the body lumen 100. The vibrating imaging catheter 2 comprises a plurality or array of ultrasound transducers 4, and a plurality of fields of view 6. The transducers 4 are placed circumferentially around the tip 2. Each transducer 4 transmits output ultrasound acoustic waves or energy in response to output or transmission electrical signals and receives reflected ultrasound energy within its field of view 6. The surface irregularity 110 of the body lumen 100 is not yet in the field of view 6 of the transducers 4.

Figure 2B:
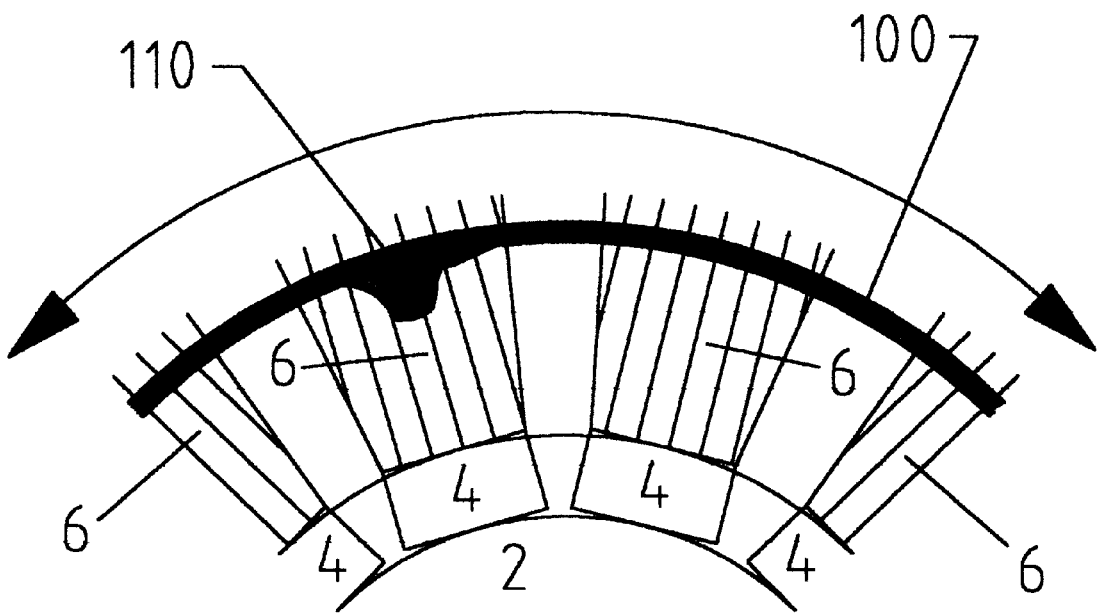

As the catheter tip 2 is rotationally vibrated, illustrated in FIG. 2B, the transducers 4 continue to transmit output ultrasound acoustic waves to and receive reflected ultrasound energy from the body lumen 100. However, each transducer 4 is rotationally vibrating and shifted from its previous position. The fields of view 6 overlap, as shown by comparing FIGS. 2A and 2B. The surface irregularity 110 of the body lumen 100 is in the field of view 6 of the transducers 4 after the catheter 2 is rotationally vibrated. When the reflection data from the transducers 4 is processed, the resulting visual image has no areas of missing information; thus resulting in a complete image which is superior to the image produced by a stationary ultrasound catheter.

Figure 3:
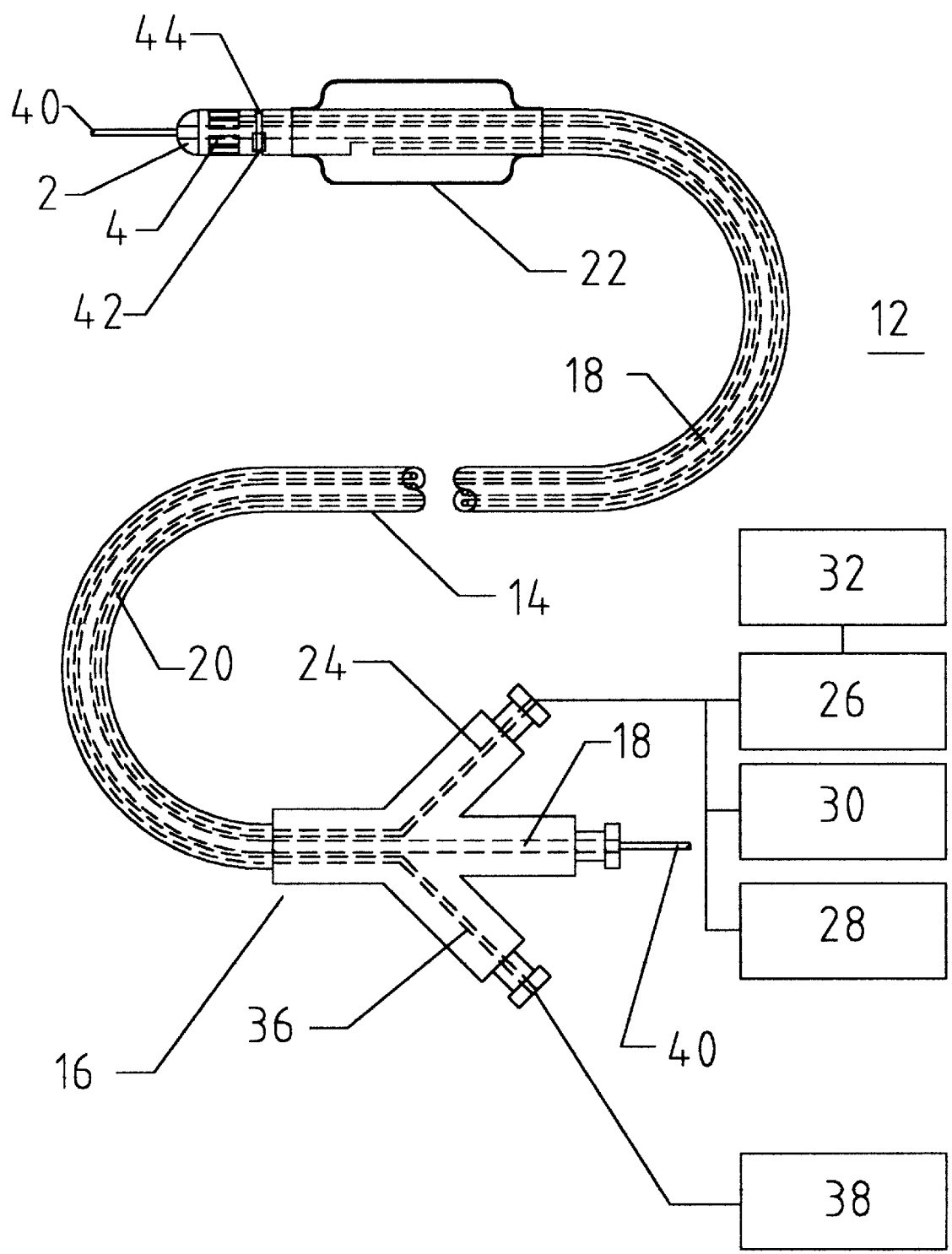
FIG. 3 is a schematic view of an intravascular ultrasound catheter.

The device of the present invention, as shown in FIG. 3, is a catheter 12 comprising a catheter shaft 14, a proximal end 16, the distal end or tip 2, a central lumen 18 and a wire bundle or transmission line 20. Additional lumens may, optionally, be added for functions such as dye or fluid injection, fluid removal, atherectomy control or balloon inflation/deflation. The proximal end 16 comprises a power/data port 24, a decoder/processor means 26, an ultrasound-input signal and power supply/controller 28, an actuator power supply/controller 30, and a display device or display monitor 32. The proximal end 16 further optionally comprises an inflation port 36, an inflation system 38, a central lumen 18, and a guidewire 40. The distal tip 2 comprises a plurality or array of ultrasound transducers 4, an actuator or, in the preferred embodiment, a nitinol actuator 42, and a swivel joint 44. The distal tip further optionally comprises the other end of the central lumen 18, the other end of the guidewire 40, and a balloon 22.

Figure 4:
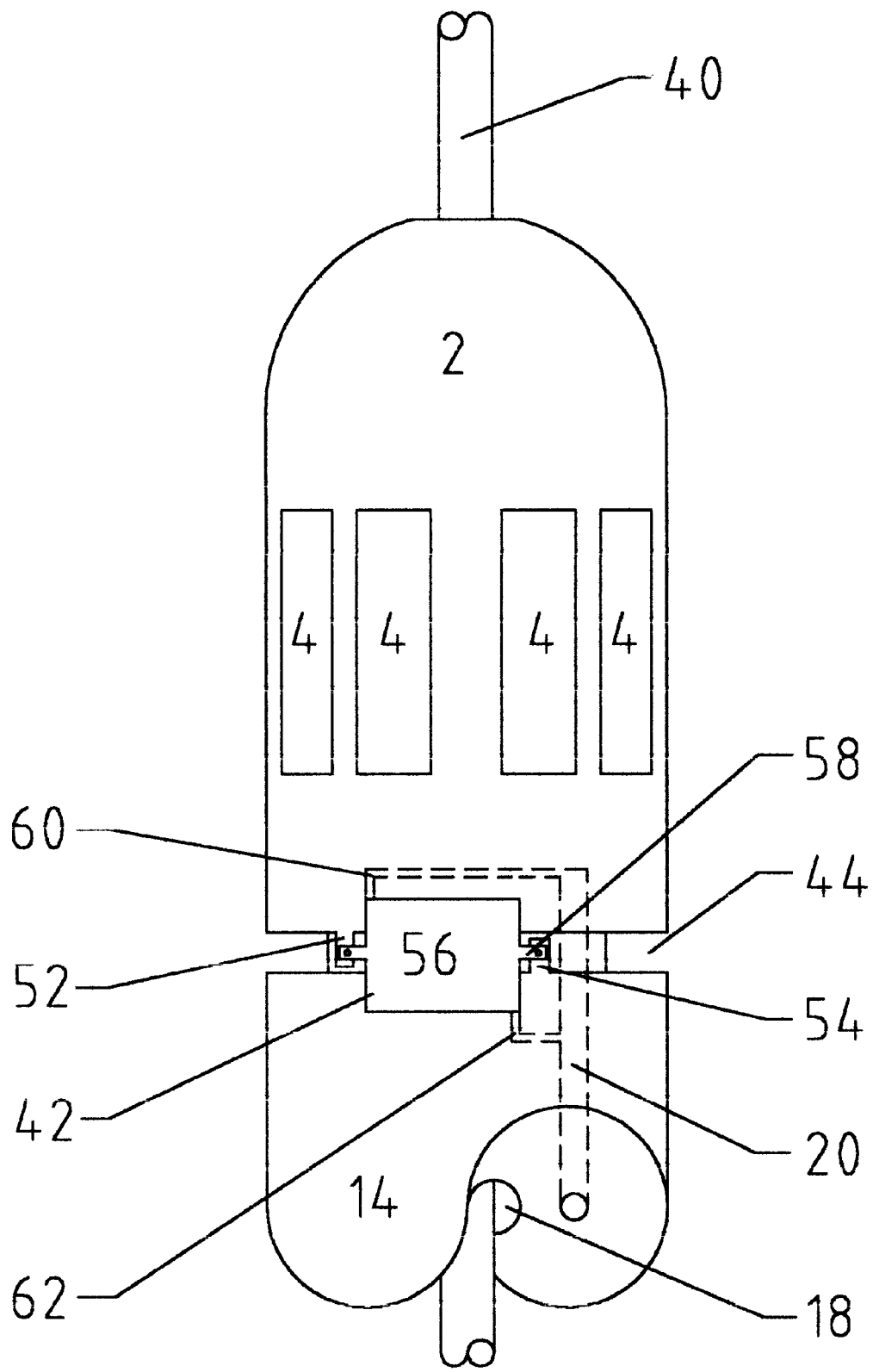
FIG. 4 is an enlarged detail of the distal tip of the imaging catheter of FIG. 3 illustrating the actuator of the preferred embodiment.
Figure 5:
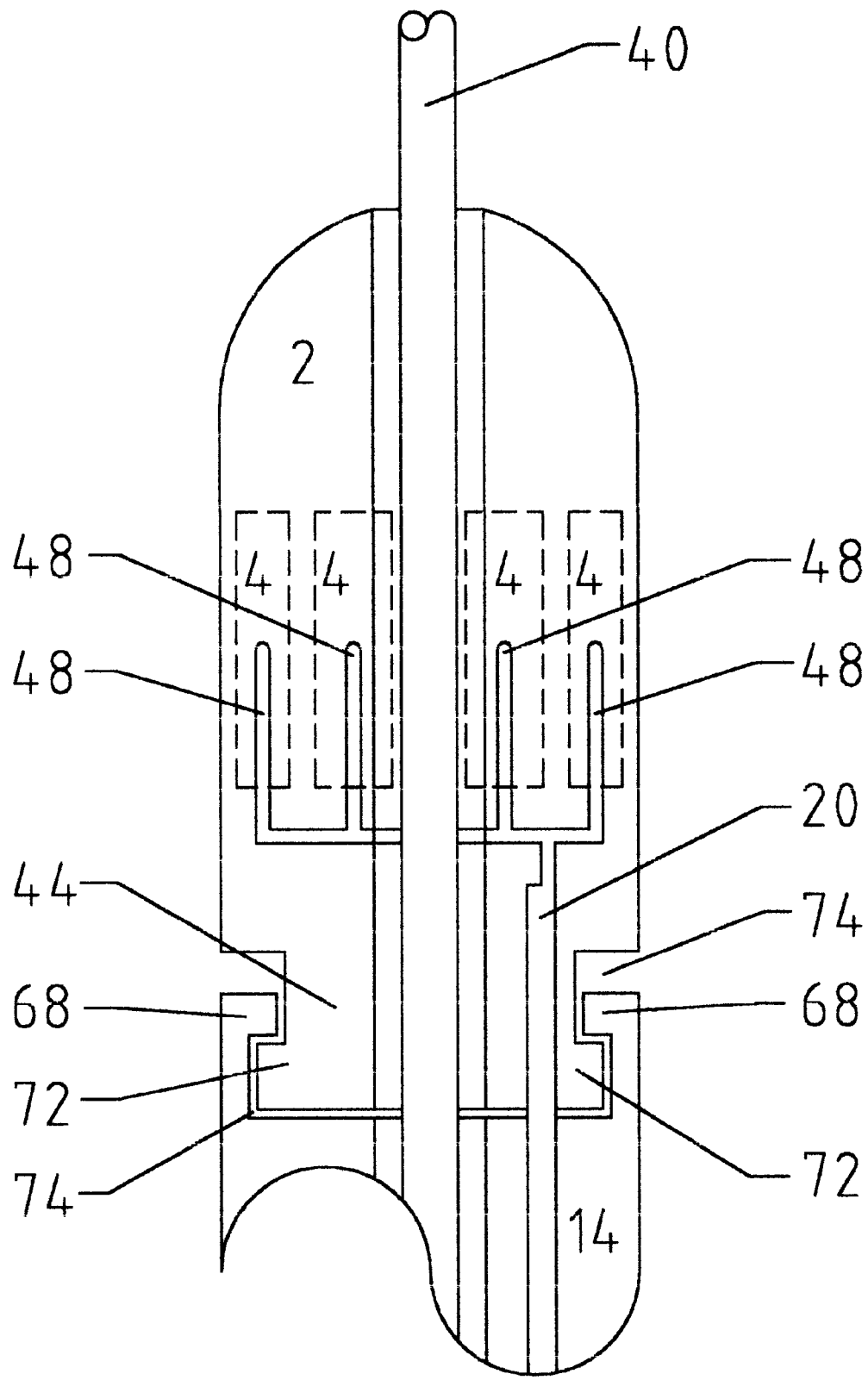
FIG. 5 is an enlarged sectional view of the distal tip of the catheter of FIG. 3 illustrating the ultrasound transducer array and the swivel connection of the preferred embodiment.

As shown in FIG. 5, each transducer in the transducer array 4 comprises a plurality of transducer leads 48 and, as shown in FIG. 4, the actuator 42 comprises a positive signal/power lead 60 and a negative signal/power lead 62. The leads 48, 60, 62 are bundled together in the wire bundle or transmission line 20 which travels the length of the catheter shaft 14 and carries power to the actuator 42 as well as output and reflection electrical signals to and from, respectively, the acoustic array 4.

Referring to FIG. 3, the catheter 12 is positioned in a body lumen or cavity to collect data for an ultrasound image. The lumen wall ideally fits against the outside of the catheter or is liquid-filled in order to efficiently transmit the acoustic waves. The ultrasound array signal and power supply/controller 28 sends output signals to and receives reflection signals from the transducer array 4 over the cable or wire bundle 20. The information from the ultrasound array 4, in the form of reflection electrical signals, is sent to the decoder/processor system 26 where the electronic data is processed to compensate for jitter, hysteresis, and uneven rotation. The processed data is sent to the display monitor 32 where the ultrasound image of the body lumen or cavity is displayed.

While the ultrasound array 4 is receiving and transmitting information, the actuator 42 is receiving control signals from the actuator power supply 30. The actuator control signals are such so as to cause the actuator 42 to rotate the distal tip 2 of the catheter 12 through an angle of 360 degrees or less and then reverse the rotation through an angle of 360 degrees or less. Once the clockwise and counterclockwise rotation cycle is complete, the cycle repeats until the desired data is collected.

In a preferred embodiment, the actuator 42 utilized to rotationally vibrate the distal tip 2 of the ultrasound-imaging catheter 12 is a nitinol actuator. Nitinol is a nickel-titanium alloy, which may exhibit a shape memory effect. Shape memory alloys (SMA) are easily deformed and when heated they return to their original shape. Shape memory actuators fabricated from thin film or wire can be heated resistively. The small thermal mass and large surface to volume ratios associated with thin films allow for rapid heat transfer. Switching rates can be in the range of up to about 100 Hz or faster.

FIG. 4 shows the distal tip 2 of the catheter 12 of FIG. 3 with the actuator means 42 of the preferred embodiment. The distal tip 2 of the catheter comprises the central lumen 18 with the guidewire 40, the ultrasound transducer array 4, the swivel joint 44, and the nitinol actuator 42. The nitinol actuator 42 comprises a mount top 52 and a mount bottom 54, a nitinol ligament/element 56, a connection or attachment 58, the positive signal/power lead 60 and the negative signal/power lead 62. The mount bottom 54 is attached to the catheter shaft 14 while the mount top 52 is attached to the catheter tip 2. The positive lead 60 and the negative lead 62 are attached to opposite edges of the nitinol ligament/ element 56, respectively.

Referring to FIG. 3 and FIG. 4, the positive lead 60 and the negative lead 62 are routed into the wire bundle or transmission line 20. The positive 60 and negative leads 62 exit the wire bundle 20 at the power/data port 24 where they are connected to the actuator power supply/controller 30. The actuator power supply/controller 30 transmits over the transmission line 20 an electrical signal through the leads 60, 62 to the nitinol ligament/element 56. This creates either resistive heating when powered or cooling when power is removed through the nitinol ligament/element 56 which causes the nitinol ligament/element to expand or contract its length along the circumference of the distal tip 2.

The nitinol ligament 56 comprises a nitinol film attached to a flexible substrate as described by R. S. Maynard in U.S. Pat. No. 5,405,337. The nitinol film is deposited onto a corrugated silicon surface coated with a thin layer of silicon nitride giving the nitinol ligaments 56 a sinusoidal shape. Polyimide is then spun on and windows are opened to expose the nitinol element. After dissolving the silicon wafer the flexible polyimide acts as a support structure for the nitinol ligaments 56. While a shape memory alloy actuator is the preferred embodiment, other actuators 42, such as those manufactured with electromagnetic or mechanically driven systems, could also be used.

Referring to FIG. 3 and FIG. 4, the actuator power controller 30 sends a signal through the positive 60 and negative leads 62 to the SMA ligament/element 56 such that the ligament/element 56 becomes heated and contracts which pulls or rotates the distal tip 2 through an angle of 360 degrees or less at the swivel joint 44. Next, the power supply/controller 30 sends a signal causing the SMA ligament/element 56 to cool and stretch, which pulls back or reverses the rotation of the distal tip 2 through the swivel joint 44. Typically heating is caused by applying power to the resistive load of the SMA element/ligament and cooling is caused by removing said power. The duty cycle of the signal is set so as to cause the SMA ligament/element 56 to continuously pull and push the distal tip 2. The resulting motion is a rotational vibration of the catheter tip 2.

In a more preferred embodiment, a plurality of nitinol actuators 42 are disposed circumferentially around the catheter tip 2. The phases of the controlling signals are adjusted such that when one nitinol actuator 42 is pulling, the opposing SMA actuator 42 is pushing. In this manner the rotational vibration of the catheter tip 2 can be made steadier and more reliable.

In another embodiment, the actuator 42 is electromagnetic, using permanent magnets and electromagnets to oscillate the catheter tip 2. This system is similar to an electric motor in that the polarities are switched on the electromagnet but continuous rotation is prevented. The electromagnetic system can be installed in the catheter tip 2 or it can transmit the energy through a torque shaft and thus be outside the body.

In yet another embodiment, a mechanical rocker linkage can be used to cause the rotational oscillations.

In another preferred embodiment the tip 2 rotates independently of the catheter shaft 14. A longitudinal section of the distal tip 2 is shown in FIG. 5. The distal tip 2 comprises the plurality or array of ultrasound transducers 4, the wire bundle 20, the guidewire 40, and the swivel connection 44. Each transducer 4 comprises leads 48 which are constrained together in the wire bundle 20. The swivel connection 44 of this embodiment comprises a shaft lip 68, a tip lip 72, and a corresponding void 74. The shaft lip 68, the tip lip 72, and the void 74 are all annular. The shaft lip 68 and tip lip 72 mate in a non-binding manner with the void 74 between the shaft lip 68 and tip lip 72. The shaft lip 68 and tip lip 72 are constructed so as to retain the distal tip 2 onto the catheter shaft 14. This results in the catheter shaft 14 retaining the catheter tip 2 but allowing the tip 2 to rotate freely on the shaft 14. The wire bundle 20 comprising the leads 48, 60, 62 passes through the above described annular swivel joint 44.

In another embodiment, the leads are connected to a swivel joint electrical rotational connector to allow for the passage of electrical signals and power through the swivel joint.

Yet another embodiment of the swivel joint 44 is an elastic segment joining the catheter shaft 14 and the catheter tip 2. This segment absorbs torque of the oscillating tip 2 and does not transmit the rotational vibration through the catheter shaft 14. The catheter shaft could optionally also include a high inertia region disposed proximal of the distal tip to stabilize the proximal portion of the catheter.

A further embodiment of the swivel joint 44 is a rotational bearing system. Additionally, the catheter 12 could be so flexible as to not require any special swivel connection. Any rotational oscillation would be damped along the length of the catheter shaft 14.

In addition to the guidewire 40 and the balloon 22, other embodiments of the catheter 12 include a linear reference transducer, and a rotational reference transducer. The balloon is used with a balloon inflation/deflation device to center the catheter 12 in a vessel lumen. The guidewire 40 is used to guide the catheter to the region to be imaged. The linear reference transducer is used when performing a three dimensional pullback image of the vessel lumen. It allows for accurate determination of location axially along the lumen.

Further, the rotational reference transducer may be used to measure the rotational displacement between the catheter shaft 14 and the catheter tip 2. An embodiment is a Hall effect switch or other magnetic device where part of the device is attached to the catheter tip 2 and the remaining part of the device is attached to the catheter shaft 14. Signals are sent, via the wire bundle 20, containing tip 2 to shaft 14 displacement information. The information is processed and correlated with the ultrasound image.

The present invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning and range of equivalency of the claims are to be embraced within their scope.

What is claimed is:

1. An imaging device for emitting ultrasonic waves and providing an image in response to detection of reflections of said acoustic waves, said imaging device comprising:

an axially elongate structure adapted for insertion into a body lumen or cavity;

an array of outwardly directed transmitting transducer elements mounted to said structure for electrically generating a plurality of output ultrasonic acoustic waves;

an actuator operably connected to said structure for rotationally vibrating said array of transducer elements;

said actuator being functional to rotationally vibrate the array to intermediate radial scan positions with respect to an initial imaging position, said rotational vibration being relative to a proximal region of said elongate structure;

a cable connecting said structure to an environment external of said lumen and including at least one signal channel for transporting electrical signals;

at least one receiving transducer mounted on said structure and proximate to said array of transmitting transducer elements for receiving reflections of said output ultrasonic acoustic waves from said array of transducer elements and converting said reflection ultrasonic acoustic waves to reflection electrical signals that may be transmitted along at least one of said signal channels in said cable;

a processor responsive to said reflection electrical signals from said cable for providing imaging data from said reflection electrical signals; and a display responsive to said imaging data for providing a visual image of said body lumen or cavity and its surrounding structure.

2. The apparatus of claim 1 further comprising a rotational reference transducer whereby an angular displacement between the distal tip and the shaft of said axially elongate structure is measured when said ultrasound transducer array is rotationally vibrated.

3. The apparatus of claim 1 further comprising a linear displacement transducer for providing three dimensional pullback information.

4. The apparatus of claim 1 wherein said actuator is constructed from shape memory materials.

5. The apparatus of claim 1 wherein said actuator is comprised of nitinol.

6. The apparatus of claim 1 wherein said axially elongate structure includes a central lumen.

7. The apparatus of claim 1 wherein said axially elongate structure includes a lumen for infusing or withdrawing fluids.

8. The apparatus of claim 1 wherein said axially elongate structure includes an inflatable balloon and at least one lumen for inflation and deflation of said balloon.

9. A method of imaging characteristics of a body lumen or cavity and surrounding structure using a catheter assembly provided with an outwardly directed, radial scanning array of transducer elements and an actuator which are located at the end of a transmission line, said method comprising the steps of:

inserting said catheter assembly into said body lumen or cavity, emitting ultrasonic signals into said body lumen or cavity and surrounding structure by selectively exciting at least one of said transducers elements, rotationally oscillating said array of transducer elements to intermediate scan positions with respect to an initial imaging position, the oscillation being relative to a proximal region of the catheter, receiving reflections of said ultrasonic signals impinging on at least one of said transducer elements, converting said reflection ultrasonic signals to reflection electrical signals suitable for transmission on said transmission line, transmitting said reflection electrical signals on said transmission line to an area external to said body lumen or cavity, and processing said reflection electrical signals into image data.

10. The method of claim 9 wherein said method includes displaying said image data on a visual display.

11. A method for imaging the interior wall of a body lumen or cavity, said method comprising:

generating an ultrasonic signal using an outwardly directed, radially scanning transducer array located on a probe or catheter in said body lumen or cavity;

rotationally vibrating said transducer array using an actuator to intermediate radial scan positions with respect to an initial imaging position, the vibration being relative to a proximal portion of said probe or catheter;

receiving ultrasonic signals reflected from the interior wall of said body lumen or cavity and adjacent structures; and producing an image from the reflected signal.

12. An ultrasound imaging probe or catheter for imaging the interior of a body lumen or cavity, said probe or catheter comprising:

an outwardly directed, radial scanning, intraluminal ultrasound transducer array adapted to be located in said body lumen or cavity;

an actuator, operably connected to said catheter or probe, for rotationally vibrating said transducer array to intermediate radial scan positions with respect to an initial imaging position, said vibration being relative to a proximal region of said probe or catheter;

a receiver for receiving ultrasonic signal reflected from the interior wall of said body lumen or cavity; and a processing and display system for producing an image from the reflected ultrasonic signal, wherein the processing and display system is electrically connected to said transducer array.

13. A device of claim 12 further comprising an actuator control and power supply/controller for controlling said actuator at a predetermined rate, wherein the power supply/controller is electrically connected to the actuator.

14. The apparatus of claim 12 further comprising a linear displacement transducer for providing three dimensional pullback information.

15. The apparatus of claim 12 wherein said actuator is constructed from shape memory materials.

16. The apparatus of claim 12 wherein said actuator is comprised of nitinol.

17. The apparatus of claim 12 wherein said probe or catheter includes a central lumen.

18. The apparatus of claim 12 wherein said probe or catheter includes a lumen for infusing or withdrawing fluids.

19. The apparatus of claim 12 wherein said probe or catheter includes an inflatable balloon and at least one lumen for inflation and deflation of said balloon.

20. An outwardly directed radial scanning intraluminal ultrasound array probe or catheter;

said probe or catheter being actuator driven to rotationally vibrate to intermediate radial scan positions with respect to an initial imaging position;

said actuator being operably connected to the distal part of said catheter or probe;

said vibration being relative to a proximal region of said catheter or probe.

* * * * *